(12) United States Patent
Alvarez Guerras et al.

(10) Patent No.: US 9,636,024 B2
(45) Date of Patent: May 2, 2017

(54) SYSTEMS AND METHODS FOR ESTIMATING HEMODYNAMIC PARAMETERS FROM A PHYSIOLOGICAL CURVE IMAGE

(71) Applicants: Oscar Alvarez Guerras, Bizkaia (ES); Borja Barrachina Larraza, Victoria (ES); Pedro Berraondo Lopez, Pamplona (ES)

(72) Inventors: Oscar Alvarez Guerras, Bizkaia (ES); Borja Barrachina Larraza, Victoria (ES); Pedro Berraondo Lopez, Pamplona (ES)

( * ) Notice: Subject to any disclaimer, the term of this patent is extended or adjusted under 35 U.S.C. 154(b) by 0 days.

(21) Appl. No.: 14/982,411

(22) Filed: Dec. 29, 2015

(65) Prior Publication Data

US 2016/0110865 A1 Apr. 21, 2016

Related U.S. Application Data

(63) Continuation of application No. PCT/US2015/030401, filed on May 12, 2015.
(Continued)

(51) Int. Cl.
*A61B 5/02* (2006.01)
*A61B 5/021* (2006.01)
(Continued)

(52) U.S. Cl.
CPC ...... *A61B 5/02108* (2013.01); *A61B 5/02028* (2013.01); *A61B 5/743* (2013.01);
(Continued)

(58) Field of Classification Search
CPC combination set(s) only.
See application file for complete search history.

(56) References Cited

U.S. PATENT DOCUMENTS 5,183,051 A * 2/1993 Kraidin ................. A61B 5/029
600/500
2002/0094119 A1* 7/2002 Sahadevan ............ G06T 7/0012
382/132
(Continued)

OTHER PUBLICATIONS

Capstesia, a new APP for monitoring advanced hemodynamic Capstesia, a new APP for advanced hemodynamic monitoring, Spanish Journal of Anesthesiology and Resuscitation. Rev Esp Anestesiol Reanim. 2014; 61 (9) : 535 536.*

*Primary Examiner* — Michael Kahelin
*Assistant Examiner* — Mitchell E Alter

(57) ABSTRACT

Systems and methods for estimating hemodynamic parameters from physiological curve images. A mobile device captures pictures of a physiological monitor display, which are used to extract the relevant physiological curve and upload it to an analysis server for processing and estimation of hemodynamic parameters. In some examples, the mobile device runs a dedicated application and is Internet-connected, which in turn connects to an Internet-connected analysis server. In some further examples, the system can be implemented using any computer that is capable of taking an image, extracting a physiological curve, and uploading it to a network service for analysis. In still further examples, analysis can be performed by the mobile device instead of via a remote server.

7 Claims, 6 Drawing Sheets

Related U.S. Application Data

(60) Provisional application No. 62/004,381, filed on May 29, 2014.

(51) Int. Cl.
*A61B 5/00* (2006.01)
*G06K 9/00* (2006.01)

(52) U.S. Cl.
CPC .......... *A61B 5/748* (2013.01); *G06K 9/00476* (2013.01); *G06K 2209/05* (2013.01)

(56) References Cited

U.S. PATENT DOCUMENTS

| | | | |
|---|---|---|---|
| 2005/0187481 A1* | 8/2005 | Hatib | A61B 5/02 600/485 |
| 2015/0297105 A1* | 10/2015 | Pahlevan | A61B 5/02427 600/301 |
| 2016/0232714 A1* | 8/2016 | McGuire | G06T 19/006 |

* cited by examiner

SYSTEMS AND METHODS FOR ESTIMATING HEMODYNAMIC PARAMETERS FROM A PHYSIOLOGICAL CURVE IMAGE

CROSS REFERENCE TO RELATED APPLICATIONS

This application claims priority to U.S. Provisional Application, Ser. No. 62/004,381, filed on 29 May 2014, and to copending Patent Cooperation Treaty Application, No. PCT/US15/30401, filed on May 12, 2015, which are hereby incorporated by reference for all purposes.

BACKGROUND

The present disclosure relates generally to utilizing software methods in the assistance of perioperative goal-directed therapy. In particular, methods of using software to calculate flow-based hemodynamic parameters useful in goal-directed therapy from images of physiological monitor traces are described.

A significant number of patients who undergo major surgery suffer postoperative complications, many of which may be avoidable. The associated health and financial loss is significant, especially considering patients who suffer from postoperative complications suffer long-term morbidity. A significant proportion of patients undergoing surgery suffer from postoperative complications, and identification of this cohort of patients may enable appropriate preventative measures to be taken. Perioperative goal-directed therapy (GDT) aims to match the increased oxygen demand incurred during major surgery, by flow-based hemodynamic monitoring and therapeutic interventions to achieve a predetermined hemodynamic endpoint. When carried out early, in the right patient cohort, and with a clearly defined protocol, GDT has been shown to reduce postoperative mortality and morbidity. Despite this, postoperative GDT is not earned out widely (Cecconi et al. Critical Care 2013, 17:209).

Known methods and systems of flow-based hemodynamic monitoring are not entirely satisfactory for the range of applications in which they are employed. For example, some existing systems require sophisticated devices and involve expensive single-use catheters. Existing systems also require specialized sensing devices, such as electrodes, probes, or transducers, to monitor the relevant hemodynamic responses.

Conversely, the prevalence of mobile devices in the health care work environment, which typically possess relatively high processing power, can run custom-developed applications, and are Internet-connected an thus able to access online processing facilities, otters a relatively untapped resource that can be employed in health-care situations to supplement or potentially replace traditional dedicated and expensive devices.

Thus, there exists a need for methods and systems that improve upon and advance the design of known methods or flow-based hemodynamic monitoring. Examples of new and useful systems and methods relevant to the needs existing in the field are discussed below.

SUMMARY

The present disclosure is directed to systems and methods for estimation of hemodynamic parameters from physiological curve images. In some examples, the systems and methods include an Internet-connected mobile device running a dedicated app, which in turn connects to an Internet-connected analysis server. The mobile device is equipped with a camera for capturing pictures of a physiological monitor display, which can then be cropped in the app on the mobile device to extract the relevant physiological curve and upload it to the analysis server for processing and estimation of hemodynamic parameters. In some further examples, the system can be implemented using any computer that is capable of taking an image, extracting a physiological curve, and uploading it to a network service for analysis. In still further examples, analysis can be performed by the mobile device instead of via a remote server.

DETAILED DESCRIPTION

The disclosed methods and systems will become better understood through review of the following detailed description in conjunction with the figures. The detailed description and figures provide merely examples of the various inventions described herein. Those skilled in the art will understand that the disclosed examples may be varied, modified, and altered without departing from the scope of the inventions described herein. Many variations are contemplated for different applications and design considerations; however, for the sake of brevity, each and every contemplated variation is not individually described in the following detailed description.

Throughout the following detailed description, examples of various methods and systems are provided. Related features in the examples may be identical, similar, or dissimilar in different examples. For the sake of brevity, related features will not be redundantly explained in each example. Instead, the use of related feature names will cue the reader that the feature with a related feature name may be similar to the related feature in an example explained previously. Features specific to a given example will be described in that particular example. The reader should understand that a given feature need not be the same or similar to the specific portrayal of a related feature in any given figure or example.

Various disclosed examples may be implemented using electronic circuitry configured to perform one or more functions. For example, with some embodiments of the invention, the disclosed examples may be implemented using one or more application-specific integrated circuits (ASICs). More typically, however, components of various examples of the invention will be implemented using a programmable computing device executing firmware or software instructions, or by some combination of purpose-specific electronic circuitry and firmware or software instructions executing on a programmable computing device.

Figure 1:
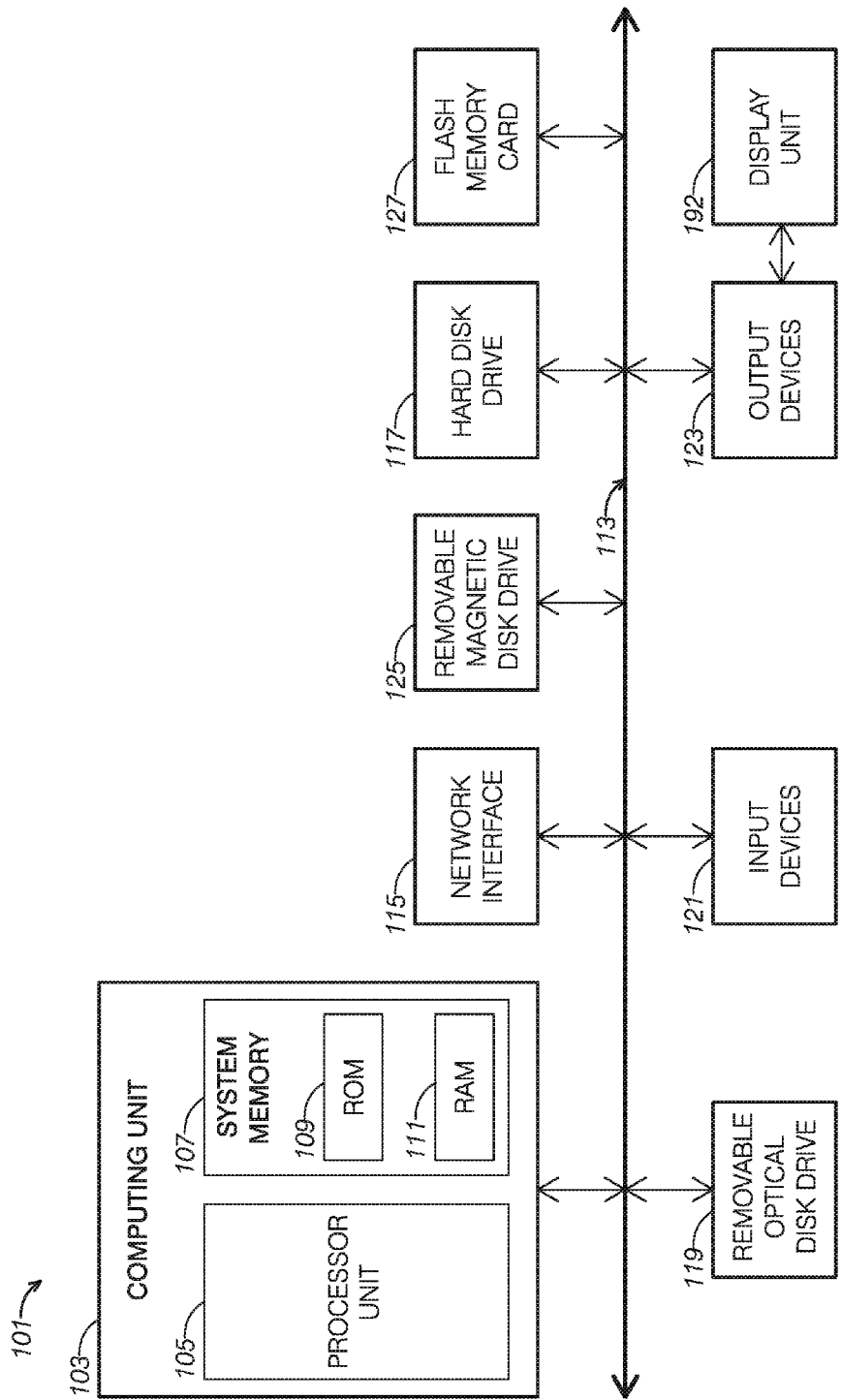
FIG. 1 shows a schematic view of an example or a programmable computing device.

Accordingly, FIG. 1 shows one illustrative example of a computer, computer 101, that can be used to implement various embodiments of the invention. Computer 101 may be incorporated within a variety of consumer electronic devices, such as personal media players, cellular phones, smart phones, personal data assistants, global positioning system devices, and the like.

As seen in this figure, computer 101 has a computing unit 103. Computing unit 103 typically includes a processing unit 105 and a system memory 107. Processing unit 105 may be any type of processing device for executing software instructions, but will conventionally be a microprocessor device. System memory 107 may include both a read-only memory (ROM) 109 and a random access memory (RAM) 111. As will be appreciated by those of ordinary skill in the art, both read-only memory (ROM) 109 and random access memory (RAM) 111 may store software instructions to be executed by processing unit 105.

Processing unit 105 and system memory 107 are connected, either directly or indirectly, through a bus 113 or alternate communication structure to one or more peripheral devices. For example, processing unit 105 or system memory 107 may be directly or indirectly connected to additional memory storage, such as a hard disk drive 117, a removable optical disk drive 119, a removable magnetic disk drive 125, and a flash memory card 127. Processing unit 105 and system memory 107 also may be directly or indirectly connected to one or more input devices 121 and one or more output devices 123. Input devices 121 may include, for example, a keyboard, touch screen, a remote control pad, a pointing device (such as a mouse, touchpad, stylus, trackball, or joystick), a scanner, a camera or a microphone. Output devices 123 may include, for example, a monitor display, an integrated display, television, printer, stereo, or speakers.

Still further, computing unit 103 will be directly or indirectly connected to one or more network interfaces 115 for communicating with a network. This type of network interface 115, also sometimes referred to as a network adapter or network interface card (NIC), translates data and control signals from computing unit 103 into network messages according to one or more communication protocols, such as the Transmission Control Protocol (TCP), the Internet Protocol (IP), and the User Datagram Protocol (UDP). These protocols are well known in the art, and thus will not be discussed here in more detail. An interface 115 may employ any suitable connection agent for connecting to a network, including, for example, a wireless transceiver, a power line adapter, a modem, or an Ethernet connection.

It should be appreciated that, in addition to the input, output and storage peripheral devices specifically listed above, the computing device may be connected to a variety of other peripheral devices, including some that may perform input, output and storage functions, or some combination thereof. For example, the computer 101 may be connected to a digital music player, such as an IPOD® brand digital music player or iOS or Android based smartphone. As known in the art, this type of digital music player can serve as both an output device for a computer (e.g., outputting music from a sound file or pictures from an image file) and a storage device.

In addition to a digital music player, computer 101 may be connected to or otherwise include one or more other peripheral devices, such as a telephone. The telephone may be, for example, a wireless "smart phone," such as those featuring the Android or iOS operating systems. As known in the art, this type of telephone communicates through a wireless network using radio frequency transmissions. In addition to simple communication functionality, a "smart phone" may also provide a user with one or more data management functions, such as sending, receiving and viewing electronic messages (e.g., electronic mail messages, SMS text messages, etc.), recording or playing back sound files, recording or playing back image files (e.g., still picture or moving video image files), viewing and editing files with text (e.g., Microsoft Word or Excel files, or Adobe Acrobat files), etc. Because of the data management capability of this type of telephone, a user may connect the telephone with computer 101 so that their data maintained may be synchronized.

Of course, still other peripheral devices may be included with or otherwise connected to a computer 101 of the type illustrated in FIG. 1, as is well known in the art. In some cases, a peripheral device may be permanently or semi-permanently connected to computing unit 103. For example, with many computers, computing unit 103, hard disk drive 117, removable optical disk drive 119 and a display are semi-permanently encased in a single housing.

Still other peripheral devices may be removably connected to computer 101, however. Computer 101 may include, for example, one or more communication ports through which a peripheral device can be connected to computing unit 103 (either directly or indirectly through bus 113). These communication ports may thus include a parallel bus port or a serial bus port, such as a serial bus port using the Universal Serial Bus (USB) standard or the IEEE 1394 High Speed Serial Bus standard (e.g., a Firewire port). Alternately or additionally, computer 101 may include a wireless data "port," such as a Bluetooth® interface, a Wi-Fi interface, an infrared data port, or the like.

It should be appreciated that a computing device employed according various examples of the invention may include more components than computer 101 illustrated in FIG. 1, fewer components than computer 101, or a different combination of components than computer 101. Some implementations of the invention, for example, may employ one or more computing devices that are intended to have a very specific functionality, such as a digital music player or server computer. These computing devices may thus omit unnecessary peripherals, such as the network interface 115, removable optical disk drive 119, printers, scanners, external hard drives, etc. Some implementations of the invention may alternately or additionally employ computing devices that are intended to be capable of a wide variety of functions, such as a desktop or laptop personal computer. These computing devices may have any combination of peripheral devices or additional components as desired.

In many examples, computers may define mobile electronic devices, such as smartphones, tablet computers, or portable music players, including wearable devices such as Google® Glass or other mobile computing platforms that are easily attached to or carried on one's person, often operating the iOS, Symbian, Windows-based (including Windows Mobile and Windows 8), or Android operating systems.

Figure 2:
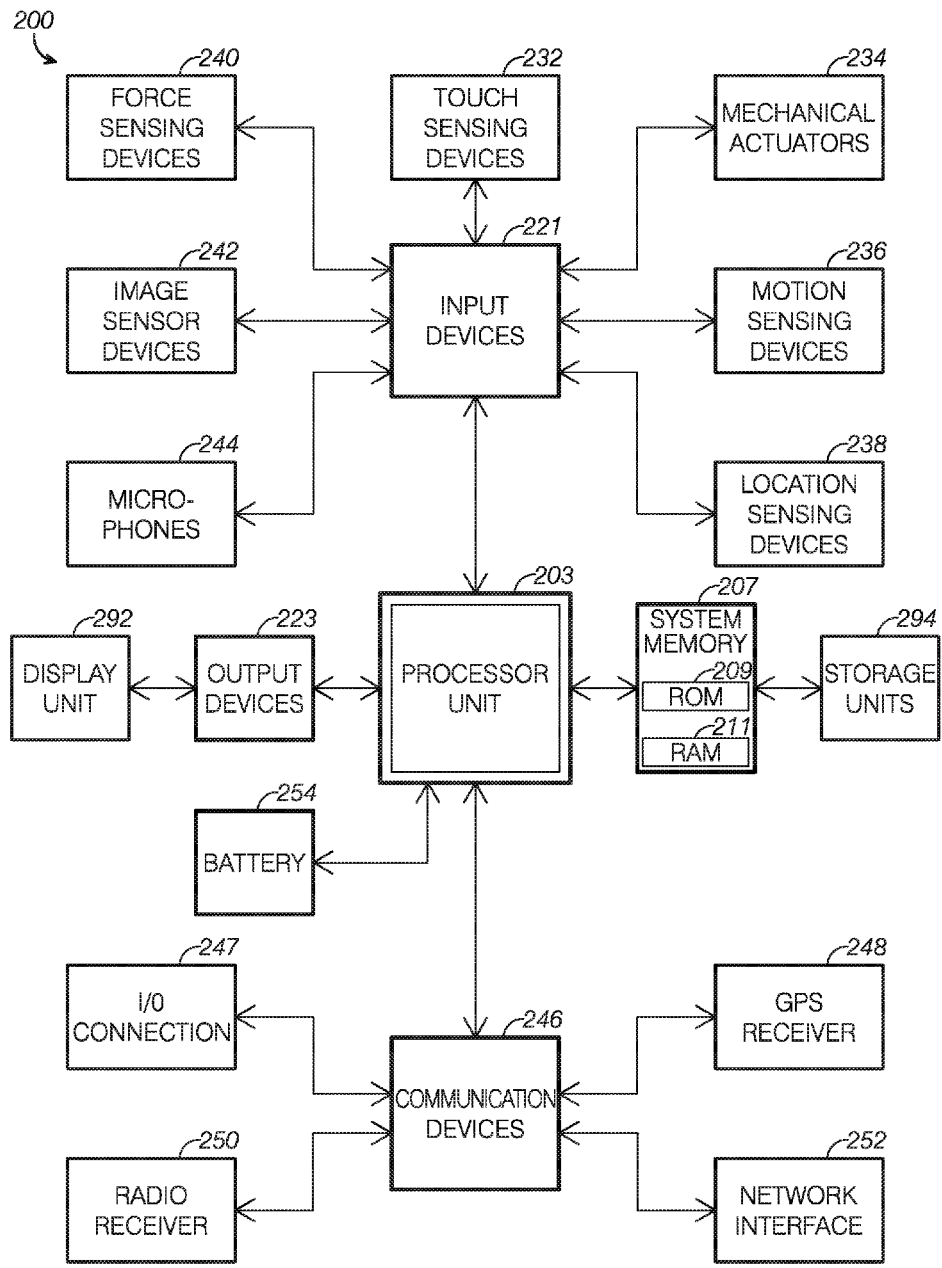
FIG. 2 shows a schematic view of an example of a mobile electronic device.

With reference to FIG. 2, an exemplary mobile device, mobile device 200, may include a processor unit 203 (e.g., CPU) configured to execute instructions and to carry out operations associated with the mobile device. For example, using instructions retrieved for example from memory, the controller may control the reception and manipulation of input and output data between components of the mobile device. The controller can be implemented on a single chip, multiple chips or multiple electrical components. For example, various architectures can be used for the controller, including dedicated or embedded processor, single purpose processor, controller, ASIC, etc. By way of example, the controller may include microprocessors, DSP, A/D converters, D/A converters, compression, decompression, etc.

In most cases, the controller together with an operating system operates to execute computer code and produce and use data. The operating system may correspond to well known operating systems such iOS, Symbian, Windows-based (including Windows Mobile and Windows 8), or Android operating systems, or alternatively to special purpose operating system, such as those used for limited purpose appliance-type devices. The operating system, other computer code and data may reside within a system memory 207 that is operatively coupled to the controller. System memory 207 generally provides a place to store computer code and data that are used by the mobile device. By way of example, system memory 207 may include read-only memory (ROM) 209, random-access memory (RAM) 211. Further, system memory 207 may retrieve data from storage units 294, which may include a hard disk drive, flash memory, etc. In conjunction with system memory 207, storage units 294 may include a removable storage device such as an optical disc player that receives and plays DVDs, or card slots for receiving mediums such as memory cards (or memory sticks).

Mobile device 200 also includes input devices 221 that are operatively coupled to processor unit 203. Input devices 221 are configured to transfer data from the outside world into mobile device 200. As shown, input devices 221 may correspond to both data entry mechanisms and data capture mechanisms. In particular, input devices 221 may include touch sensing devices 232 such as touch screens, touch pads and touch sensing surfaces, mechanical actuators 234 such as button or wheels or hold switches, motion sensing devices 236 such as accelerometers, location detecting devices 238 such as global positioning satellite receivers, WiFi based location detection functionality, or cellular radio based location detection functionality, force sensing devices such as force sensitive displays and housings, image sensors, and microphones. Input devices 221 may also include a clickable display actuator.

Mobile device 200 also includes various output devices 223 that are operatively coupled to processor unit 203. Output devices 233 are configured to transfer data from mobile device 200 to the outside world. Output devices 233 may include a display unit 292 such as an LCD, speakers or jacks, audio/tactile feedback devices, light indicators, and the like.

Mobile device 200 also includes various communication devices 246 that are operatively coupled to the controller. Communication devices 246 may, for example, include both an I/O connection 247 that may be wired or wirelessly connected to selected devices such as through IR, USB, or Firewire protocols, a global positioning satellite receiver 248, and a radio receiver 250 which may be configured to communicate over wireless phone and data connections. Communication devices 246 may also include a network interface 252 configured to communicate with a computer network through various means which may include wireless connectivity to a local wireless network, a wireless data connection to a cellular data network, a wired connection to a local or wide area computer network, or other suitable means for transmitting data over a computer network.

Mobile device 200 also includes a battery 254 and possibly a charging system. Battery 254 may be charged through a transformer and power cord or through a host device or through a docking station. In the cases of the docking station, the charging may be transmitted through electrical ports or possibly through an inductance charging means that does not require a physical electrical connection to be made.

The various aspects, features, embodiments or implementations of the invention described above can be used alone or in various combinations. The methods of this invention can be implemented by software, hardware or a combination of hardware and software. The invention can also be embodied as computer readable code on a computer readable medium. The computer readable medium is any data storage device that can store data which can thereafter be read by a computer system, including both transfer and non-transfer devices as defined above. Examples of the computer readable medium include read-only memory, random access memory, CD-ROMs, flash memory cards, DVDs, magnetic tape, optical data storage devices, and carrier waves. The computer readable medium can also be distributed over network-coupled computer systems so that the computer readable code is stored and executed in a distributed fashion.

Figure 3:
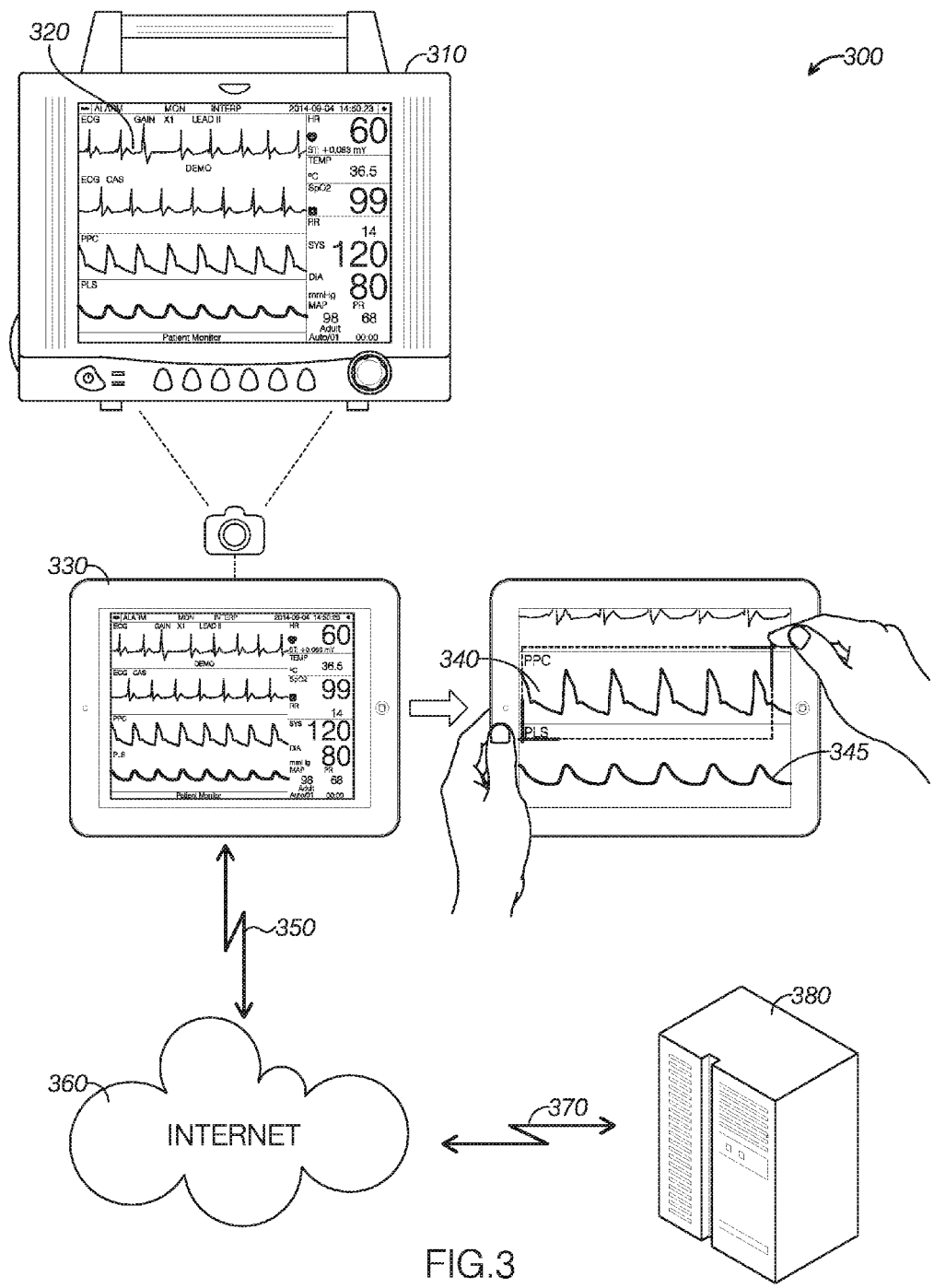
FIG. 3 is a diagram of the components of an example system for estimation of hemodynamic parameters from a physiological curve image.
Figure 4:
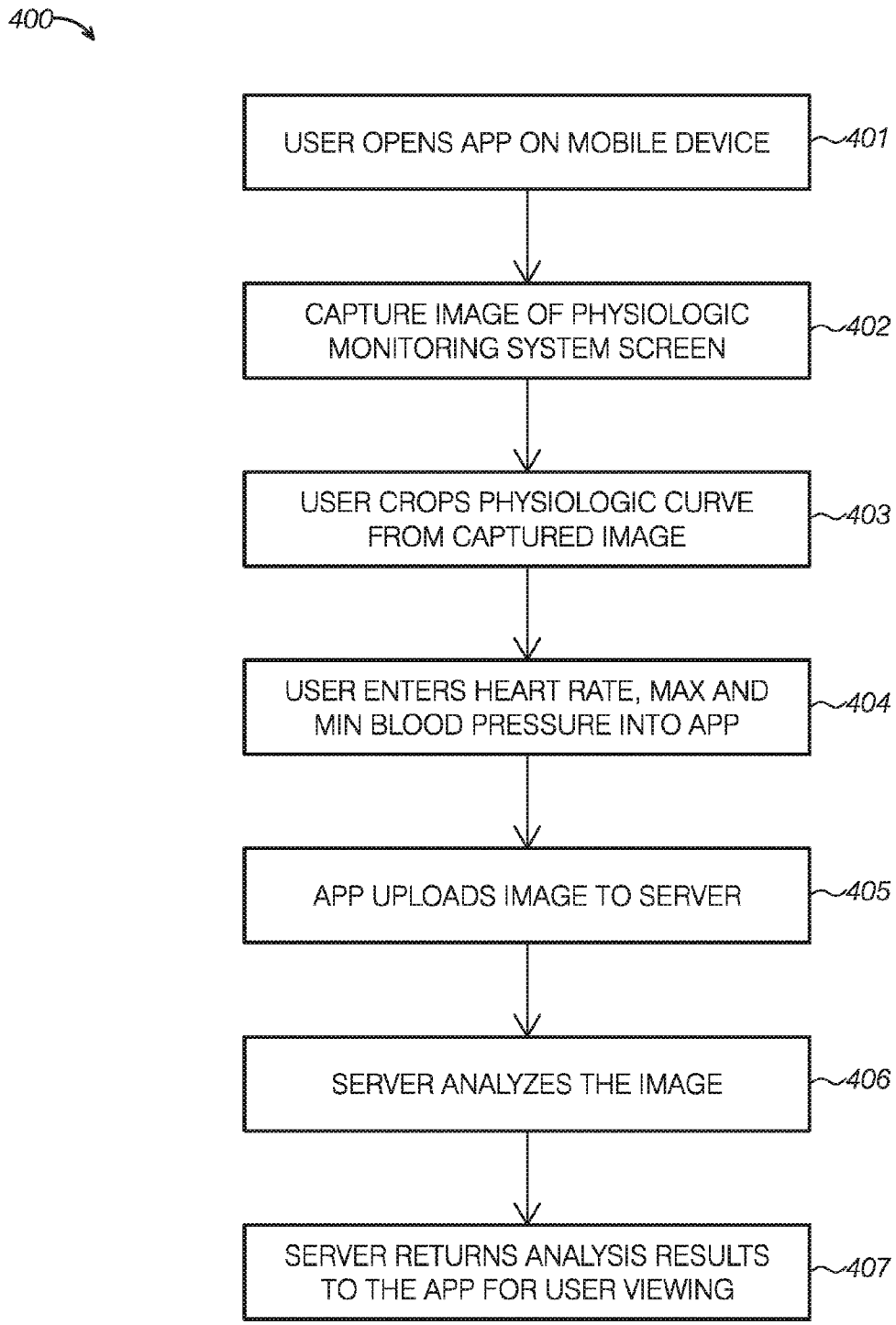
FIG. 4 is a chart of the steps a user takes to utilize an example system for estimation of hemodynamic parameters from a physiological curve image.

With reference to FIGS. 3 and 4, an example of a system, system 300, will now be described. System 300 includes a physiologic monitor 310 that includes a display 320, a mobile device 330 that includes a camera, and an analysis server 380 in data communication via network connections 350 and 370 through the Internet 360 with the mobile device 330. System 300 functions to implement the method 400 outlined in FIG. 4, as described in steps 401 through 407.

The example system 300 implementing method 400 addresses many of the shortcomings existing with conventional systems and methods. For example, by utilizing an image captured from a physiologic monitor 310, analysis and computation of hemodynamic parameters is accomplished without the need for additional specialized sensors or catheters. The data is acquired by second hand use (via image capture) of existing sensors employed by a commonly deployed physiologic monitor 310. Furthermore, the use of an app downloaded onto the mobile device 330, typically a smartphone or tablet that is common in the workplace, can significantly reduce the costs associated with specialized equipment, and make deployment much more widespread than otherwise possible with purpose-dedicated equipment.

The mobile device 330 is ideally a device such as an iPhone, iPod or iPad from Apple Inc., a phone, tablet, or other device running the Android operating system from Google, a mobile phone or tablet that runs a version of Microsoft Windows (either for phone or a version of Windows depending on the hardware equipment utilized), or any other mobile device and corresponding operating system that is now known or may be developed in the future. The mobile device 330 is preferably equipped with a built-in camera to allow for easy capture of an image of the display 320 of physiologic monitor 310. In a preferred implementation of the system 300, the mobile device 330 runs an application that facilitates capture of the physiologic monitor display 320, allows either manual cropping of a physiologic curve including a pulse pressure curve 340 or a plethysmographic curve 345, as shown in FIG. 3, or automatic curve extraction, and can upload the physiologic curve to analysis server 380. The mobile device 330 communicates with the analysis server 380 over a network connection. As depicted in FIG. 3, this network connection 350 may communicate via the Internet 360, where the analysis server 380 is remotely located ("cloud"-based), and is also capable of two-way communication via a network connection 370 to the Internet.

The mobile device 330 could alternatively be implemented using any computing platform that is capable of receiving a captured image of a physiological monitor display 320, cropping the image of the display 320 to extract a physiologic curve, and communicating with the analysis server 380 to send the curve and receive results.

Referring to FIG. 4, an example of a method for estimation of hemodynamic parameters from a physiologic monitor image including either a pulse pressure curve 340 or a plethysmographic curve 345 will now be described through its steps of operation. In step 401, a user with a mobile device equipped with a camera, e.g. smartphone, iPod, iPad, tablet, or similar such device, opens the app that has previously been loaded on the device. Next, in step 402 the user uses the mobile device's camera to take a picture of the screen of a physiologic monitoring system that includes either a pulse pressure curve 340 or a plethysmographic curve 345. The app can automatically select the curve if it is in red. This is accomplished by subtracting the color image from a grayscale version of the image multiplied by a factor that is ideally 0.85, and then selecting the biggest region that contains a red element. Alternatively, the user in step 403 may directly crop the curve from the image. This is depicted in FIG. 3, where the mobile device 330's touch display is used by the user with cropping brackets to select the relevant physiological curve 340. Alternatively, automatic selection can be performed by the analysis server 380. In such an implementation, the mobile device 330 would skip step 404 and, after capture in step 402 and entry of parameters in step 404 (described below), upload the uncropped image of display 320 to the analysis server 380, which would perform step 403 in automatic fashion as described above before engaging in analysis.

In step 404, the user optionally supplies the heart rate, maximum blood pressure, and minimum blood pressure, which are used by the system to estimate cardiac output. If these parameters are not supplied, only the pulse pressure variation will be computed. Once cropping and parameter entry is complete, the app uploads the image to an analysis server 380 in step 405. The analysis server 380 analyzes the image, step 406, which will be described in greater detail with reference to FIG. 5, and finally in step 407, the analysis server 380 returns the analysis results to the app for viewing and utilization by the user. Upon receiving the results, the user can check the analysis quality by viewing the computed hemodynamic parameters and graphs based on the parameters generated by the app or, optionally, the analysis server 380. Users can also plot the time series of the different parameters, and calculate derivative parameters such as the cardiac index.

FIG. 3 depicts the analysis server 380 as being located on the Internet 360. It will be understood by a practitioner skilled in the relevant art that the analysis server 380 can also be implemented using an Internet-based cloud service, a remotely placed server, or a server placed locally on a network owned by the care facility utilizing the disclosed invention. Having a cloud-based implementation perform the analysis provides benefits such as simplification of the software requirements on the mobile device 330, generally increased analysis speed, and ease of keeping the analysis software up-to-date. Such analysis server 380, if not implemented in a cloud-based manner, can be implemented using dedicated, discrete computer hardware of suitable specifications, or in a virtualized server environment. Alternatively, for locations where a continuous network connection is not feasible, and given a mobile device 330 of suitable processing power, the app itself could perform the analysis locally on the mobile device 330, obviating the need for an analysis server 380.

Figure 5:
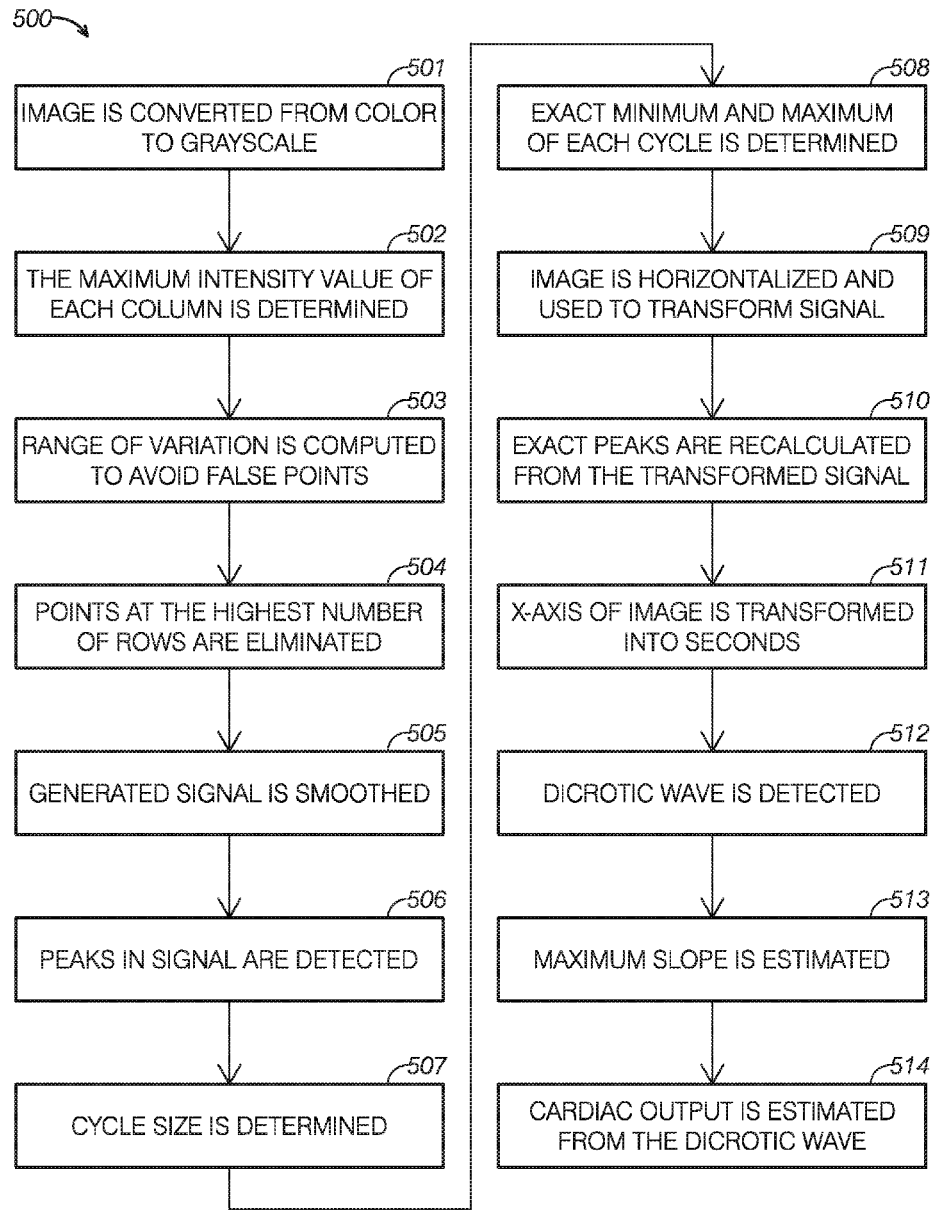
FIG. 5 is a chart of the analysis steps performed by an example system for estimation of hemodynamic parameters from a physiological curve image.

Turning to FIG. 5, analysis method 500, the processing steps taken by the analysis server 380 in analyzing a suitable physiologic curve, will now be described. To analyze the uploaded image, a two-dimensional signal must be extracted, with the x-axis being the time of the pulse pressure curve, and the y-axis being the pressure level. To do this, the two-dimensional image is analyzed with respect to columns of pixels. Following upload of the physiological curve image, in step 501 the image is converted from color to grayscale to simplify analysis. Alternatively, a single channel of color, e.g. the red channel, could be utilized it conversion to grayscale is not feasible. This step simplifies each pixel in the image to a single numeric value representing its intensity, with lower values representing darker pixels, and higher values corresponding to brighter, higher intensity pixels. In steps 502, 503, and 504 the physiological curve signal is obtained by determining the pixel of maximum intensity value in each column of the image (also and interchangeably referred to herein as a "point" along the pulse pressure curve signal). This is accomplished by analyzing the first column of the image and determining which row contains the pixel with the highest value. Next, in step 502 false high points are avoided by taking the number of rows in the image and multiplying that number by a suitable constant, thereby creating a subset window above and below the row location of the maximum intensity value in which to choose the maximum intensity value for the next pixel column. Finally, in step 504 any points at the highest value of the number of rows are eliminated. An example of this method being applied will better demonstrate its operation: if the image to be analyzed has 600 rows, a subset window of 120 (600*0.2) would be utilized. If the pixel of maximum intensity value in column one is located in row 252, only the pixels in rows 132 through 372 of the second column (252+/−120) will be evaluated, and the pixel of maximum intensity will be selected from that range. For the third column, the pixels in the rows+/−120 from the row of the pixel of maximum intensity selected in the second column will be evaluated, and so forth until all columns have been evaluated, resulting in an x-y signal representative of the physiological curve. Note that a multiplier of 0.2 was used in this example; this value was empirically determined to optimize performance of the analysis. However, it will be appreciated that there are a range of values that will work, and depending on the cleanliness and quality of the image to be analyzed, different values may yield more accurate results. The multiplier may either be preset into the system or made user-adjustable if greater user control over the performance of the image analysis is desired. These parameters may also be preset with several value sets that are tuned to achieve optimal results depending on whether a pulse pressure curve or a plethysmographic curve is utilized.

Once the physiological curve x-y signal is obtained, peak detection is performed. In step 505 two smoothed signals are generated from the original signal, the first using a 50-point average, and the second using a three-point average. The averaging values of 50 and three points were determined empirically to be optimal; however, a range of values are usable, and these values may be made user-adjustable if the ability for the user to fine-tune the performance of the analysis is desired. Peak detection in step 506 is carried out by first analyzing the 50-point smoothed signal. It a given point value is higher than the points of the five preceding columns and the five succeeding columns it is considered a peak. The value of five for preceding and succeeding columns is empirically determined, and may be varied to tune the efficiency of peak detection. The size of each physiological cycle is calculated in step 507 by taking the mean of the differences between two peaks. Next, in step 508 the 3-point smoothed signal is searched for the maximum value that is located between each peak detected in step 506+/−the size of the cycle between the peaks determined in step 507, divided by 2. Then, the signal is searched for a minimum value between each peak minus the size of the physiological cycle divided by 2, and minus the physiological cycle divided by 3 and the peak plus the size of the physiological cycle divided by 2. The angle of a line drawn through the peaks is calculated, and used in step 509 to horizontalize the three-point smoothed signal. Finally, the exact peak locations are determined from the horizontalized three-point smoothed signal in step 510.

Further considering FIG. 5, the signal's x-axis is transformed into seconds in step 511 by first dividing the user-supplied heart rate into the associated time interval in seconds to obtain the time of each beat in seconds (e.g. if the heart rate is expressed in beats per minute, then the appropriate calculation would be to divide 60 by the heart rate; if the entered heart rate was 80 bpm, the calculation would be 60 seconds per minute/80 bpm=0.75 seconds per beat). This figure is then divided by the average distance in pixel columns between two cycles, to yield the seconds value of each pixel column. Continuing with the above example, if the average distance between cycles was 30 pixel columns, then the appropriate calculation would be 0.75 seconds per beat/30 pixels per beat=0.025 seconds per pixel column.

Next, in step 512 the location of the dicrotic wave is detected by rotating the descending segment of each cycle, and applying a rotation that allows detection of a minimum point that is at least a specified minimum distance from the end of the descending cycle segment. To determine the appropriate angle of rotation, the signal is iteratively rotated and analyzed until an angle is employed that results in the dicrotic wave appearing as a minimum point located at least the specified minimum distance from the end of the descending cycle segment. To speed up computation time, rotations may optionally be limited to 30 degrees, 45 degrees, and 50 degrees, which have been empirically determined to yield useful results. The specified minimum distance is preferably half the length of the descending segment, but may optionally be set by the user should user control over algorithm fine tuning be desired. In step 513 the maximum slope of the descending segment of each cycle is computed by determining the angle between two points that are ideally 20 pixel columns apart. This number has been determined to yield good results when employed on signals of varying quality that may result for varying quality source images. However, it can be made user-adjustable if greater user control over the analysis performance is desired.

Finally, in step 514 the cardiac output is estimated by determining the area under each cycle up to the dicrotic wave and dividing the result by 500. Prior art implementations use several points extracted from pulse pressure signals to determine this area. However, it has been determined empirically that simply using a constant achieves an accurate estimate while cutting down on analysis complexity. The constant of 500 has been determined to yield good results, but this value could be made user adjustable should greater control over analysis performance be desired.

Finally, the server returns the result to the user via the app, as detailed above in the description of FIG. 4.

Figure 6A:
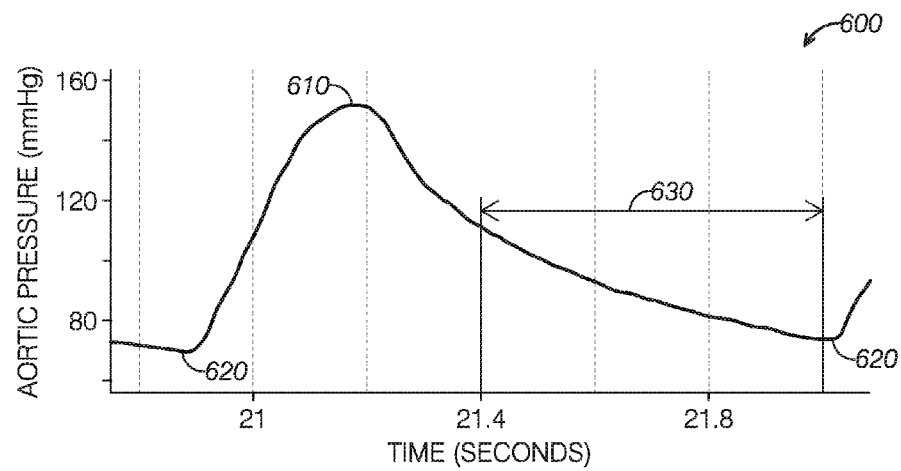
FIGS. 6A and 6B are close-ups of example physiological curves that are analyzed by an example system for estimation of hemodynamic parameters.
Figure 6B:
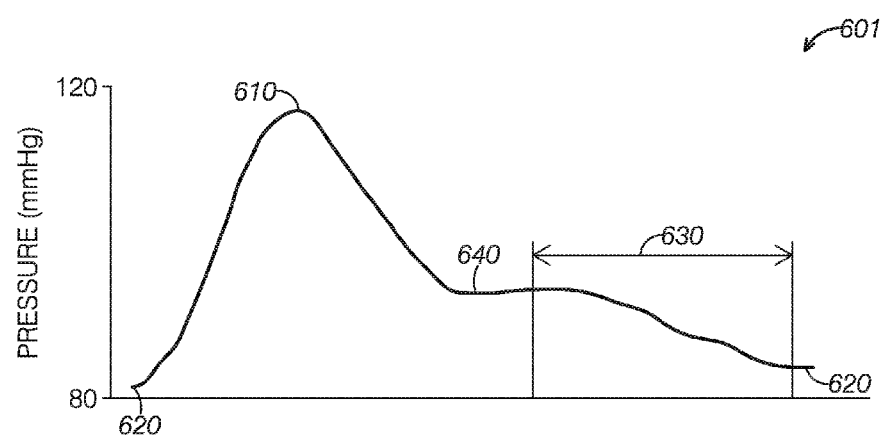

Turning attention to FIGS. 6A and 6B, two examples of physiological curves 600 and 601 such as would be useful in analysis method 500 are depicted. Both curves include a peak 610 and minimums 620. The dicrotic wave, used in method 500 to estimate cardiac output, is shown as range 630 in each example curve. In physiological curve 600, the dicrotic wave range 630 is seen as the portion following the peak where the curve transitions to a shallow decay from the initial steep drop coming from peak 610, and lasts until the second minimum 620, which marks the start of a new wave cycle. In physiological curve 601, a dicrotic notch 640 is clearly visible, which can be detected to help connote the start of the dicrotic wave range 630.

It will be understood by a practitioner skilled in the relevant art that the foregoing steps of the image analysis would be performed directly by the app on the mobile device when used in an implementation of the disclosed invention that does not rely upon a cloud service or separate server.

The foregoing methods can be adapted to analyze a video clip of a physiologic monitor's pulse pressure curve, as opposed to a single picture, by first extracting a frame from the video for analysis. In such an implementation, the extracted frame serves as the still image to be analyzed, with the frame either selected automatically by software, or by the user. The above-mentioned analysis parameters and constants can be adjusted as necessary to optimize analysis of a plethysmographic waveform as needed.

INDUSTRIAL APPLICABILITY

The inventions described in this application may be made by a variety of industrial processes, including by various mechanical, electrical and software development techniques. Further, the inventions described herein may be used in industrial contexts, including improving health and patient care delivery endeavors.

The inventions described above may be alternatively described according to the following non-limiting embodiments:

In a first embodiment for a system, the system may include a physiologic monitor attached to a patient, an Internet-connected mobile device equipped with a camera capable of capturing an image of the physiologic monitor display, and a corresponding Internet-connected analysis server capable of communicating with the mobile device for analyzing the display image and returning analysis results to the mobile device.

In some example methods of the first embodiment for the system, the mobile device allows the user to crop out the relevant portion of the display image, specifically a physiological curve, and then supplies the extracted curve to the analysis server. The server analyzes the extracted curve to determine relevant hemodynamic parameters, which are then supplied back to the mobile device. In other examples, the mobile device may be programmed to automatically extract the relevant curve, or the analysis server may perform automatic curve extraction. In yet other example embodiments, the mobile device itself may perform all extraction and analysis, without reliance on a separate network-connected server.

The disclosure above encompasses multiple distinct inventions with independent utility. While each of these inventions has been disclosed in a particular form, the specific embodiments disclosed and illustrated above are not to be considered in a limiting sense as numerous variations are possible. The subject matter of the inventions includes all novel and non-obvious combinations and subcombinations of the various elements, features, functions and/or properties disclosed above and inherent to those skilled in the art pertaining to such inventions. Where the disclosure or subsequently filed claims recite "a" element, "a first" element, or any such equivalent term, the disclosure or claims should be understood to incorporate one or more such elements, neither requiring nor excluding two or more such elements.

Applicant(s) reserves the right to submit claims directed to combinations and subcombinations or the disclosed inventions that are believed to be novel and non-obvious. Inventions embodied in other combinations and subcombinations of features, functions, elements and/or properties may be claimed through amendment of those claims or presentation of new claims in the present application or in a related application. Such amended or new claims, whether they are directed to the same invention or a different invention and whether they are different, broader, narrower or equal in scope to the original claims, are to be considered within die subject matter of the inventions described herein.

The invention claimed is:

1. A system for flow-based hemodynamic monitoring, comprising:
    a display device configured to visually display a physiological curve of a patient, the physiological curve comprising either a pulse pressure curve or a plethysmographic curve;
    a capture device comprising:
        a camera configured to capture the visual display of the physiological curve of the patient;
        capture storage media containing a capture set of instructions configured to be executed by the capture device, the capture set of instructions including instructions for enabling a user to manually extract an extracted portion of the visual display containing the physiological curve from the visual display; and
        a capture communication device configured to transmit and receive image information, the image information including the extracted portion of the visual display portion containing the physiological curve; and
    an analysis device configured to analyze the extracted portion of the visual display containing the physiological curve transmitted from the capture device to determine one or more hemodynamic parameters.

2. The system of claim 1, wherein the capture set of instructions contained in the capture storage media further comprise instructions for automatically extracting the extracted portion of the visual display containing the physiological curve from the visual display.

3. The system of claim 1, wherein the analysis device comprises:
    analysis storage media containing an analysis set of instructions configured to be executed by the analysis device, the analysis set of instructions including instructions for:
        generating a physiological curve signal from the extracted portion of the visual display;
        determining peaks in the physiological curve signal; and
        using the peaks to determine a cycle size of the physiological curve signal;
        determining a location of a dicrotic wave in the physiological curve signal;
        calculating a calculated area under a curve for each cycle of the physiological curve signal up to the dicrotic wave of the physiological curve signal; and
        using the calculated area to calculate an estimate of cardiac output; and
    an analysis communication device configured to transmit and receive analysis information, the analysis information including the extracted portion of the visual display containing the physiological curve and the one or more hemodynamic parameters.

4. The system of claim 3, wherein the analysis device further comprises a server.

5. The system of claim 3, wherein the analysis device is configured to operate in an Internet-connected cloud service mode.

6. The system of claim 5, wherein the capture device is a mobile device configured to connect to the Internet and to communicate with the analysis device operating in the Internet-connected cloud service mode.

7. The system of claim 6, wherein the analysis set of instructions further comprises instructions for transmitting to the mobile device over the Internet the one or more hemodynamic parameters.

* * * * *